US009051585B2

(12) United States Patent
Bell

(10) Patent No.: US 9,051,585 B2
(45) Date of Patent: Jun. 9, 2015

(54) PROCESS FOR THE PRODUCTION OF ALCOHOLS

(75) Inventor: Peter Bell, Dunblane (GB)

(73) Assignee: INEOS SALES (UK) LIMITED, Lyndhurst, Hampshire (GB)

( * ) Notice: Subject to any disclaimer, the term of this patent is extended or adjusted under 35 U.S.C. 154(b) by 1185 days.

(21) Appl. No.: 12/452,208

(22) PCT Filed: Jun. 12, 2008

(86) PCT No.: PCT/EP2008/057407
§ 371 (c)(1),
(2), (4) Date: Dec. 22, 2009

(87) PCT Pub. No.: WO2009/010347
PCT Pub. Date: Jan. 22, 2009

(65) Prior Publication Data
US 2010/0105118 A1    Apr. 29, 2010

(30) Foreign Application Priority Data
Jul. 19, 2007   (EP) .................................... 07252869

(51) Int. Cl.
| C12P 3/00 | (2006.01) |
| C01B 3/38 | (2006.01) |
| C12P 7/06 | (2006.01) |
| C12P 7/02 | (2006.01) |

(52) U.S. Cl.
CPC ... *C12P 3/00* (2013.01); *C12P 7/02* (2013.01); Y02E 50/32 (2013.01); *C01B 3/382* (2013.01); C01B 2203/0233 (2013.01); C01B 2203/0238 (2013.01); C01B 2203/0405 (2013.01); C01B 2203/06 (2013.01); C01B 2203/1235 (2013.01); C01B 2203/142 (2013.01); *C12P 7/065* (2013.01); Y02E 50/17 (2013.01)

(58) Field of Classification Search
None
See application file for complete search history.

(56) References Cited

U.S. PATENT DOCUMENTS

| 4,122,110 | A |  | 10/1978 | Sugier et al. |
| 4,752,623 | A |  | 6/1988 | Stevens et al. |
| 4,780,481 | A |  | 10/1988 | Courty et al. |
| 4,831,060 | A |  | 5/1989 | Stevens et al. |
| 5,593,886 | A |  | 1/1997 | Gaddy |
| 5,807,722 | A |  | 9/1998 | Gaddy |
| 5,821,111 | A |  | 10/1998 | Grady et al. |
| 6,090,312 | A |  | 7/2000 | Ziaka et al. |
| 2003/0211585 | A1 |  | 11/2003 | Gaddy et al. |
| 2007/0275447 | A1 |  | 11/2007 | Lewis et al. |
| 2008/0057554 | A1 |  | 3/2008 | Huhnke et al. |
| 2008/0115415 | A1 | * | 5/2008 | Agrawal et al. .................. 48/101 |

FOREIGN PATENT DOCUMENTS

| WO | WO 98/00558 A1 | 1/1998 |
| WO | WO 00/68407 A1 | 11/2000 |
| WO | WO 02/08438 A2 | 1/2002 |
| WO | WO 03/051803 A1 | 6/2003 |
| WO | WO 2007/003909 A1 | 1/2007 |
| WO | WO 2008/002538 A2 | 1/2008 |
| WO | WO 2008/028055 A2 | 3/2008 |

OTHER PUBLICATIONS

Turk et al. "Novel Technologies for Gaseous Contaminants Control" DOE Contract No. DE-AC26-99FT40675, Research Triangle Institute Research Triangle Park, NC 27709 Sep. 2001, 112 pages.*
Rostrup-Nielsen "New aspects of syngas production and use" Catalysis Today 63 (2000) 159-164.*
Xu et al. "Methane Steam Reforming, Methanation and Water-Gas Shift: 1. Intrinsic Kinetics" AIChE Journal, Jan 1989, vol. 35, No. 1, pp. 88-96.*
Snoeck et al. "Steam/CO2 Reforming of Methane. Carbon Filament Formation by the Boudouard Reaction and Gasification by CO2, by H2, and by Steam: Kinetic Study" Ind. Eng. Chem. Res. 2002, 41, 4252-4265.*
Tsipouriari et al. "Kinetic study of the catalytic reforming of methane with carbon dioxide to synthesis gas over Ni/La2O3 catalyst" Catalysis Today 64 (2001) 83-90.*
"Bench-scale Demonstration of Biological Production of Ethanol from Coal Synthesis Gas" *Bioengineering Resources, Inc.*; U.S. Department of Energy (DOE) Reports, pp. 1-18 (1995).
PCT International Preliminary Report on Patentability, mailed Jan. 28, 2010; International Application No. PCT/EP2008/057407, International Filing Date Jun. 12, 2008 (8 pgs).
Nirula, Satish C.; PEP Review No. 85-1-4; "Dow/Union Carbide Process for Mixed Alcohols from Syngas"; *Process Economics Reviews*; pp. 1-4, 8 (Figure 4.1) and 11 (Table 4.2) (Dec. 1985).
Arora, D., et al; "Production of Ethanol from Refinery Waste Gases"; Final Report, 96 pgs, Apr. 1999-Jul. 1997D.
Christensen, T.S., et al; Petrochemical/Chemical Developments, "Improve Syngas Production Using Autothermal Reforming, Flexible process design uses partial oxidation and adiabatic-steam reforming to cut costs"; *Hydrocarbon Processing*, (6 pgs), Reprinted from Mar. 1994.
Madsen, Sandra E.L. Winter, et al; "Industrial Aspects of $CO_2$-reforming"; Haldor Topsoe A/S, Denmark, pp. 1-10, Jan. 1997.

(Continued)

*Primary Examiner* — Thane Underdahl
(74) *Attorney, Agent, or Firm* — Nixon & Vanderhye P.C.

(57) ABSTRACT

Process for producing C2+ alcohols from a methane-containing feedstock, by passing the methane-containing feedstock and $CO_2$ to a non-oxidative reforming process to produce a product stream containing CO, $H_2$ and $CO_2$, optionally in the presence of steam, provided that where steam is present in the feed to the reforming process, the steam and $CO_2$ are present in a molar ratio of less than 5:1. The CO, $H_2$ and $CO_2$ stream is passed to a bacterial fermentation step where it is converted to a liquid product stream containing one or more C2+ alcohols and a gaseous product stream containing CO, $H_2$ and $CO_2$. The fermentation step is operated to provide a conversion of CO of at least 60%. CO, $H_2$ and $CO_2$ are recycled from the gaseous product stream to the reforming process such that the $H_2$ reacts with carbon dioxide in the reforming process.

12 Claims, 1 Drawing Sheet

(56) References Cited

OTHER PUBLICATIONS

Dibbern, H.C., et al; "Make low $H_2$/CO syngas using sulfur passivated reforming"; *Hydrocarbon Processing*; pp. 71-74, Jan. 1986.

Song, Xueping, et al; "Technologies for direct production of flexible $H_2$/CO synthesis gas"; *Energy Conversion and Management*; vol. 47, No. 5, pp. 560-569, Mar. 2006.

Udengaard, N.R., et al; "Sulfur passivated reforming process lowers syngas $H_2$/CO ratio"; *Oil & Gas Journal*, pp. 62-67, Mar. 1992.

Song, Zueping, et al; "Technologies for direct production of flexible $H_2$/CO synthesis gas"; *Energy Conversion and Management*, vol. 47, pp. 560-569 (2006).

Teuner, ST. C., et al; "CO through $CO_2$ Reforming—The Calcor Standard and Calcor Economy Processes"; *Oil Gas European Magazine*, pp. 44-46, Mar. 2001.

"Bench-scale Demonstration of Biological Production of Ethanol from Coal Synthesis Gas"; Topical Report 5: Process Analysis; Submitted by Bioengineering Resources, Inc., Fayetteville, AR, , pp. 1-19, Nov. 1995.

"Final Report High Pressure Synthesis Gas Conversion"; Prepared by University of Arkansas, Dept. of Chemical Engineering, Fayetteville, AR, 72 pgs, Published May 1993.

Henstra, A.M., et al; "Microbiology of synthesis gas fermentation for biofuel production"; *Current Opinion in Biotechnology*; vol. 18, pp. 200-206 (2007).

Lewis, R.S., et al; "Fermentation of producer gas-effects of "contaminants"", (poster); 1 pg, 2004.

Kusel, K., et al; "Clostridium scatologenes strain SL I isolated as an acetogenic bacterium from acidic sediments", (abstract only); *International Journal of Systematic and Evolutionary Microbiology*, vol. 50, pp. 537-546, Copyright by Society for General Microbiology (2000).

Sipma, J.; "Microbial Hydrogenogenic CO conversions: applications in synthesis gas purification and biodesulfurization"; (Abstract and p. 37-38 from dissertation), Jan. 4, 2006.

\* cited by examiner

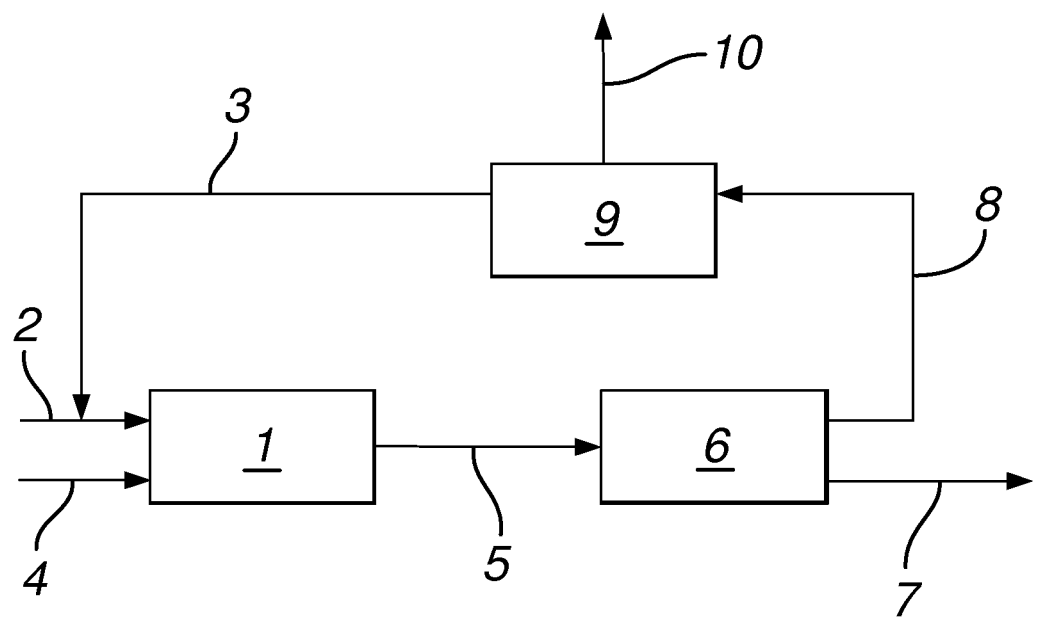

PROCESS FOR THE PRODUCTION OF ALCOHOLS

This application is the U.S. national phase of International Application No. PCT/EP2008/057407 filed 12 Jun. 2008 which designated the U.S. and claims priority to European Application No. 07252869.8 filed 19 Jul. 2007, the entire contents of each of which are hereby incorporated by reference.

The present invention relates to a process for the production of one or more C2+ alcohols. In particular, the present invention relates to a process for the production of one or more C2+ alcohols from a methane-containing feedstock via formation of carbon monoxide and hydrogen and subsequent fermentation of the carbon monoxide and hydrogen to one or more C2+ alcohols.

BACKGROUND OF THE INVENTION

The production of alcohols from carbon oxides and hydrogen is well-known in the art. For example, a number of processes are known which use catalysts which are known to catalyse the reaction, including those based on Group VI metals, especially molybdenum, as described, for example in U.S. Pat. No. 4,752,623 and U.S. Pat. No. 4,831,060, and those based on mixed metal oxides, especially based on copper and cobalt containing catalysts, as described, for example, in U.S. Pat. No. 4,122,110 and U.S. Pat. No. 4,780,481. More recent publications include WO 2007/003909 A1, which also describes a process for the conversion of carbon oxide(s) and hydrogen containing feedstocks into alcohols in the presence of a particulate catalyst.

The catalytic routes generally produce a mixed alcohols product slate, including methanol, ethanol and heavier alcohols, especially propanol and butanols. The selectivity to the various alcohol products depends on the particular catalyst and process conditions employed and, although both methanol and the higher alcohols (ethanol and above) are usually formed in any particular reaction, the art generally seeks to maximise either methanol or the higher alcohols at the expense of the other.

There are also known processes for the conversion of carbon monoxide and hydrogen into C2+ alcohols based on fermentation processes using bacteria. Examples of fermentation processes can be found, for example, in WO 02/08438 and WO 00/68407, and are also described in DOE reports under DOE Contract Number DE-AC22-92PC92118, such as "Bench-scale Demonstration of Biological Production of Ethanol from Coal Synthesis Gas", Topical Report 5, November 1995.

In general such processes are much more selective for specific alcohols, such as ethanol, compared to catalytic processes, with much lower quantities, if any, of other alcohols being formed.

The carbon monoxide and hydrogen for such processes can be obtained by reforming of methane-containing feedstocks, such as natural gas, to produce a mixture of carbon monoxide, hydrogen and carbon dioxide (synthesis gas). A number of methane reforming processes and variants thereon are known in the art, principally:

(1) steam methane reforming (SMR), in which the methane containing feedstock is reformed in an externally fired reformer in the presence of >2:1 molar steam:methane ratio (usually >2.5:1), (2) autothermal reforming (ATR), in which the methane containing feedstock is reformed in the presence of steam and oxygen, and (3) partial oxidation (PDX), in which the methane containing feedstock is reformed in the presence of oxygen and relatively low or zero concentrations of steam Significant variations on the above 3 processes are also known, and thus, for example, carbon dioxide can be added to steam methane reforming or autothermal reforming to adjust the ratio of hydrogen to carbon monoxide obtained. In a particular example, dry gas reforming is a variation of steam methane reforming in which the methane containing feedstock is reformed in the presence of significant concentrations of carbon dioxide and low or zero concentration of feed steam—the feed $CO_2$ has the effect of reducing the $H_2$:CO ratio and the low water content allows more effective conversion of $CO_2$ to CO.

In general, however, the ratio of hydrogen to carbon monoxide obtained is decreased in the order (1)>(2)>(3), with a typical SMR reformer (1) having an $H_2$:CO molar ratio of approximately 4.5:1 versus 2:1 for an ATR reformer (2) and 1.7 or 1.8:1 for a PDX reformer (3). (Unless stated otherwise, all ratios herein are molar ratios)

Each of the above processes also produces carbon dioxide. As well as the highest carbon monoxide to hydrogen ratios, ATR and PDX also result in the lowest carbon dioxide and methane in the resulting synthesis gas. Typically an SMR produces syngas with a molar ratio of $CO_2$:CO in the region of 0.35:1 versus 0.2:1 for an ATR and <0.1:1 for a PDX.

In theory, both catalytic and fermentation routes to higher alcohols (ethanol and heavier alcohols) may utilise $CO_2$ as a reactant for the production of the higher alcohols. However, in practise, both catalytic and fermentation routes to higher alcohols tend to be net producers of carbon dioxide.

In the case of catalytic conversions, such reactions may utilise the carbon dioxide via "direct" conversion or via co-occurrence of the water-gas shift reaction, $CO_2+H_2$ ↔ $CO+H_2O$. However, whilst for methanol production, the production can occur directly from $CO_2$, most higher alcohol catalysts appear only to be able to react $CO_2$ via the shift reaction, and at the typical higher alcohol catalyst operating conditions of 250-400° C., the shift equilibrium favours $CO_2$ over CO—and results in the net production of $CO_2$ over the catalyst.

In the case of fermentation routes, the bacteria used for fermentation can produce alcohols according to either of the following 2 reactions $$6CO + 3H_2 \rightarrow C_2H_5OH + 4CO_2$$

$$2CO_2 + 6H_2 \rightarrow C_2H_5OH + 3H_2O$$

However, the CO conversion is typically 70-90% per pass while the $H_2$ conversion is typically less than the CO conversion—therefore the fermentation is also a net producer of $CO_2$.

Based on the above, it may be expected that where fermentation is used to produce alcohols from synthesis gas, such processes would operate most favourably with synthesis gas with the highest concentrations of carbon monoxide and lowest proportion of $CO_2$ to CO, which would favour ATR and PDX over SMR.

SUMMARY OF THE INVENTION

However, it has now been found that, contrary to this expectation, the integrated process for the production of C2+ alcohols from a methane-containing feedstock via intermediate formation of synthesis gas and subsequent fermentation operates most effectively with reforming in the absence of oxygen.

Thus, in a first embodiment, the present invention provides a process for the production of C2+ alcohols from a methane-containing feedstock, which process comprises:
 a. passing said methane-containing feedstock and carbon dioxide to a non-oxidative reforming process to produce a first product stream comprising CO, $H_2$ and $CO_2$, optionally in the presence of steam, but with the proviso that where steam is present in the feed to the reforming process the steam and $CO_2$ are present in a molar ratio of less than 5:1,
 b. passing the first product stream comprising CO, $H_2$ and $CO_2$ to a bacterial fermentation step wherein it is converted to produce a second product stream comprising one or more C2+ alcohols in the liquid phase and a gaseous third product stream comprising CO, $H_2$ and $CO_2$, the fermentation step being operated to provide a conversion of CO of at least 60%,
wherein CO, $H_2$ and $CO_2$ are recycled from the gaseous third product stream to the reforming process of step (a).

The present invention provides a process for the production of C2+ alcohols. "C2+ alcohols" as defined herein, means ethanol and heavier alcohols, especially C2 to C6 alcohols, and most preferably C2 to C4 alcohols i.e. ethanol, propanol and butanols (iso-butanol and n-butanol). C2+ alcohols can also be generally referred to as "higher alcohols".

In the process of the present invention, carbon dioxide and hydrogen in the product stream from the fermentation process is utilised as at least a portion of the feed to the reforming process. The reforming process is either in the substantial absence of steam, in which case it may be considered as dry-gas reforming, or a limited amount of steam is utilised, but with the proviso that where steam is also present in the feed to the reforming process the steam and $CO_2$ are present in a molar ratio of less than 5:1 (unless otherwise stated, as used herein all quantities and ratios are in moles).

ATR and PDX processes generally produce a higher proportion of carbon monoxide to carbon dioxide and would be expected to be a better fit with a fermentation process which is more effective at converting carbon monoxide/water than carbon dioxide/hydrogen to ethanol. However, it has now been found that when the fermentation system is integrated with an ATR or a PDX unit, the system operates in hydrogen deficit and results in a build-up of carbon dioxide in the process. This carbon dioxide results in larger recycles with their associated energy use and the net result is that carbon dioxide ends up needing to be purged from the system giving increased net carbon dioxide production and poorer feedstock selectivity to the desired C2+ alcohol product.

In contrast, the integrated process of the present invention operates with a hydrogen excess and efficiently converts the carbon dioxide in the feed to the reforming process to carbon monoxide, and actually results in a lower process inventory of carbon dioxide. The present invention thus significantly reduces the net carbon dioxide production through 3 mechanisms:
 1. The excess hydrogen is reacted in the reformer with the $CO_2$ to form CO and water (the CO can be fermented to ethanol rather than $CO_2$ emitted to atmosphere)
 2. The lower inventory of $CO_2$ results in less energy use in the recycle stream
 3. The reduction in steam use in the reformer reduces the reformer heating duty In particular, it is possible to recycle all the $CO_2$ from the fermentation reaction to the reformer and still operate the system in hydrogen excess.

The present invention also takes advantage of the fact that bacterial fermentation of synthesis gas to alcohols can be operated with relatively high carbon monoxide conversion, such that the product stream has a relatively low amount of carbon monoxide in it. This means that carbon monoxide can be economically recycled to the earlier reforming process. In a most preferred embodiment, this avoids the need for any specific separation of carbon monoxide from carbon dioxide in the product stream prior to recycle. Preferably, the fermentation step is operated to provide a conversion of CO of at least 70%, more preferably at least 80%.

The carbon monoxide conversion in a bacterial fermentation process is the result of a combination of a number of factors that can be controlled by the operator of the process. In general, the key requirements to obtain high CO conversion (>60%) are to ensure healthy bacteria and suitable contacting of the bacteria with the reactants. For a particular bacteria this effectively means to ensure sufficient nutrients for the bacteria are provided, to ensure that the fermentation takes place in the correct temperature range, and to ensure sufficient gas contact with the bacteria, which is a function of gas pressure in the fermentation reaction, residence time in the fermentation reaction and reaction agitation.

For a particular reaction and desired production rate such factors may be optimised by the person skilled in the art. In the event that conversion falls below 60% (or a higher threshold if required), then conversion can be increased again by acting on one of these parameters as might be necessary, for example, by increasing agitation rate, thereby increasing gas contacting with the bacteria.

Typically, the selectivity (based on total CO converted and on a non $CO_2$ basis) to higher alcohols of the fermentation process is at least 60%, especially at least 75%, and most preferably at least 90%. ($CO_2$ is a net reaction product in the conversion of CO to ethanol e.g. $6CO+3H_2O \rightarrow C_2H_5OH+ 4CO_2$. Selectivity on a non $CO_2$ basis relates to the conversion of CO to ethanol compared to methanol or alkanes).

Suitably, at least 60% of the carbon monoxide and 60% of the carbon dioxide in the gaseous third product stream are recycled, more preferably at least 80% of the carbon monoxide and 80% of the carbon dioxide in the gaseous third product stream are recycled and most preferably at least 90% of the carbon monoxide and 90% of the carbon dioxide in the gaseous third product stream are recycled to the reforming process of step (a). (Small amounts may be lost to purges or during any hydrogen separation that might be present.)

Whilst there are numerous "claims" in the literature for "high conversion" catalytic processes for the production of alcohols from synthesis gas, it is not believed that such processes can be operated at high conversion and high selectivity to higher alcohols. In particular, as conversion is increased, the selectivity of the catalyst systems to alcohols compared to alkanes is diminished.

U.S. Pat. No. 4,831,060, for example, exemplifies only CO conversions of less than 40%. However, without high CO conversion the amount of carbon monoxide remaining in the gaseous third product stream of the present invention would be relatively high, and it would be necessary to separate at least some of the carbon monoxide from the carbon dioxide prior to recycle to maintain a driving force for $CO_2$ conversion to CO in the reforming process. This is described, for example, in SRI Report "Dow/Union Carbide Process for Mixed Alcohols from Syngas", PEP Review Number 85-1-4, in which carbon monoxide is separated from the recycle stream and recycled to the catalytic alcohols production process.

By "non-oxidative reforming process" in step (a) of the process of the present invention is meant a process in which no (molecular) oxygen is (deliberately) present in feed. Thus, autothermal reforming and partial oxidation processes are explicitly excluded from the process of the present invention. The preferred reforming processes according to the present invention are dry gas reforming and steam methane reforming (with steam limited as defined). A particularly preferred process is sulphur passivated reforming. Sulphur passivated reforming (SPARG) is described in Hydrocarbon Processing, January 1986, p. 71-74 or Oil & Gas Journal, Mar. 9, 1992, p. 62-67. In such a process, sulphur is added to passivate the reforming catalyst. The sulphur reduces coke formation, which can otherwise be a problem. It is reported that the sulphur blocks the large sites (which are required to form coke) but leave the small sites open which allow reforming to continue.

The SPARG process is not believed to have been widely utilised for formation of synthesis gas. Without wishing to be bound by theory, it is believed that this may be:
 (1) because most processes which use synthesis gas require higher $H_2$:CO ratios than are obtained by SPARG reforming, and
 (2) because sulphur is generally a catalytic poison, which means it needs to be removed prior to any subsequent processing of the synthesis gas formed.

In contrast, bacterial fermentation processes have been found to be tolerant to sulphur present in the feed. This is described, for example, in the DOE report "Bench-scale Demonstration of Biological Production of Ethanol from Coal Synthesis Gas", Topical Report 5, November 1995 (DOE Contract Number DE-AC22-92PC92118).

Not only is there no need to remove sulphur prior to the fermentation step, therefore, but the sulphur can be readily recycled in the gaseous third product stream.

Where steam is present, the preferred steam:$CO_2$ molar ratio is less than 2:1, most preferably less than 1:1. Lower steam:$CO_2$ molar ratios have been found to result in further increased efficiency in $CO_2$ conversion during the reforming step, lower steady state $CO_2$ concentration in process (as well as much lower $H_2O$), and reduced overall inventory into the process.

The non-oxidative reforming process also produces $H_2O$. Advantageously, this water may also be used as part of the fermentation medium in the subsequent fermentation step. Thus, in the process of the present invention, all the products of the synthesis gas production may be used, or at least passed to, the fermentation step, reducing the requirements for separations.

The process according to the present invention operates with excess hydrogen. In one embodiment, it is preferred to separate at least some of the hydrogen in the gaseous third product stream. As well as providing a source of a fuel gas (which can be used to power the reformer, for example, saving further energy costs) this results in a net reduction in recycle rates to the reformer. Any suitable separation technique may be utilised. A membrane, especially a hydrogen-selective membrane is most preferred.

Any suitable methane-containing feedstock may be utilised.

The most preferred feedstock is natural gas (which may or may not also include inherent quantities of carbon dioxide, nitrogen and higher hydrocarbons), but other suitable feedstocks include landfill gas, bio digester gas and associated gas from oil production and processing.

As noted previously, the present invention also takes advantage of the fact that bacterial fermentation of synthesis gas to alcohols can be operated with relatively high carbon monoxide conversion, such that the product stream has a relatively low amount of carbon monoxide in it. Not only does this mean that carbon monoxide gaseous third product stream can be economically recycled to the earlier reforming process, but the lower carbon monoxide in the feed to the reforming process favours further the conversion of carbon dioxide according to the reforming equilibrium ($CO_2+CH_4 \leftrightarrow 2CO+2H_2$).

In a most preferred embodiment, the process of the present invention is operated at elevated pressure in both the reforming and fermentation steps. Preferably the pressure is in the range 2 to 12 barg for both steps. The pressure is preferably set based on the optimum pressure for the fermentation step, and the reforming process operated at essentially the same pressure (except for small inherent pressure loss between steps) to provide the first product stream at the required pressure for the fermentation step, and with minimal compression required for the recycle of the third gaseous product stream to the reforming process. One further advantage of SPARG technology, for example, is that it may be operated across a wide range of pressures dependent on the downstream processing required without significant variations in product distribution.

The fermentation process may use any suitable bacteria. The preferred fermentation process uses acetogenic anaerobic bacteria, especially a rod-shaped, gram positive, non-thermophilic anaerobe. Useful bacteria according to this invention include *Acetogenium kivui, Acetobacterium woodii, Acetoanaerobium noterae, Clostridium Aceticum, Butyribacterium methylotrophicum, Clostridium acetobutylicum, Clostridium thermoaceticum, Eubacterium limosum, Peptostreptococcus productus, Clostridium ljungdahlii* and *Clostridium carboxydivorans*. One particularly suitable bacteria is *Clostridium carboxydivorans*, especially suitable strains being those designated "P7" and "P11". Such bacteria are described, for example, in US 2007/0275447 and US 2008/0057554. A further particularly suitable bacteria is *Clostridium ljungdahlii*, especially suitable strains being *Clostridium ljungdahlii* PETC, *Clostridium ljungdahlii* ERI2, *Clostridium ljungdahlii* C01, *Clostridium ljungdahlii* O-52. *Clostridium ljungdahlii* and processes using such bacteria are described in DOE report "Bench-scale Demonstration of Biological Production of Ethanol from Coal Synthesis Gas", Topical Report 5, November 1995 (DOE Contract Number DE-AC22-92PC92118) and in patent applications WO 98/00558, WO 00/68407 and WO 02/08438. The process generally comprises contacting the first product stream comprising CO, $H_2$ and $CO_2$ with the bacteria in the presence of a nutrient medium in a suitable reactor, for example a continuously stirred tank reactor (CSTR). Suitable temperatures and pressures can be determined by the person skilled in the art, and are dependent on the bacteria and other process conditions used, but typical temperatures for the fermentation are between 25° C. and 85° C., especially 35° C. to 45° C. and typical pressures are in the range atmospheric to 12 barg, preferably 2 to 12 barg.

"Nutrient medium" is used generally to describe conventional bacterial growth media which contain vitamins and minerals sufficient to permit growth of a selected subject bacteria. Suitable nutrients are well-known, for example as described in US 2003/211585, WO 08/00558, U.S. Pat. No. 5,807,722, U.S. Pat. No. 5,593,886 and U.S. Pat. No. 5,821,111.

The agitation rate may be selected by the person skilled in the art depending on the reaction vessel and robustness of the bacteria. In particular, the reaction mixture is generally agitated at a suitable rate to ensure adequate gas dispersion and substantial avoidance of agglomeration of dispersed gas bubbles whilst minimising damage to the bacterium cells caused by any moving parts e.g. stirrer tips.

In practise this usually means that for a larger unit agitated with a stirrer a smaller RPM (revolutions per minute) is used than for a corresponding smaller unit (for a fixed RPM, the tip speed of a larger agitator is faster than that of a smaller agitator). Speeds of 20 to 1000 RPM are typical, with larger units operating at the lower rates.

The residence time may also be selected by the person skilled in the art depending on the particulars of the reaction, and in order to obtain the desired conversion. The residence time is usually in the range 5 seconds to 20 minutes, and most typically in the range 10 seconds to 5 minutes.

Generally, the fermentation step produces a gas phase product comprising CO, $H_2$ and $CO_2$ (which fours the gaseous third product stream according to the present invention) and a liquid reaction broth comprising a mixture of fermentation bacteria, nutrients, alcohols, and by-products, such as acetic acid, in >95% water. The liquid reaction broth is usually removed from the fermenter and filtered to remove cells and other solids, then distilled to produce a more concentrated alcohol/water product mixture (which forms the second product stream according to the present invention) and a recycle stream comprising nutrients, water and acetic acid which is returned to the fermenter.

BRIEF DESCRIPTION OF THE DRAWINGS

The invention will now be described with respect to FIG. 1, which shows in schematic form a process for the production of alcohols from a methane-containing feedstock according to the process of the present invention.

In particular, FIG. 1 shows a non-oxidative reforming process (1) to which is passed a methane-containing feedstock (2) and a recycle stream (3) comprising carbon dioxide, carbon monoxide and hydrogen. Steam, if required, may be provided through line (4). Reforming of the methane-containing feedstock occurs to produce a first product stream (5) comprising CO, $H_2$ and $CO_2$, which is passed to a bacterial fermentation step (6) wherein it is converted in the presence of a suitable bacteria to produce a second product stream (7) comprising one or more alcohols in the liquid phase and a gaseous third product stream (8) comprising CO, $H_2$ and $CO_2$, the fermentation step being operated to provide a conversion of CO of at least 60% (Separations steps in the fermenter not shown). The gaseous third product stream (8) comprising CO, $H_2$ and $CO_2$ is passed to a membrane separator (9) wherein a portion of the hydrogen therein is separated (10), to leave a stream comprising carbon dioxide, carbon monoxide and the remaining hydrogen which is recycled as stream (3). A small purge (not shown) is also taken to prevent build-up of inerts such as nitrogen and argon in the recycle stream.

EXAMPLES

Integrated processes for reforming and fermentation according to FIG. 1 have been modelled using Aspen.:
the reformer is modelled as an equilibrium reactor with the SMR specified with an outlet temperature of 945° C. and the ATR specified with an outlet temperature of 1030° C. The following reactions are modelled within the fermenter

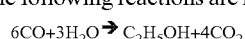

In the present Examples, a $H_2$ conversion of half that of the CO conversion is used, providing a net reaction of

The CO conversion used is 90%

All modelling assumes a net methane input to the process of 100 kmoles per hour and, for simplicity, zero moles of inert gases such as nitrogen or argon (in reality, some proportion of these will always be present in the methane), and seeks to produce approximately 40 kmoles per hour of ethanol.

Comparative Example

In this Example, an autothermal reformer is used. A feed of methane (100 kmoles per hour) and a recycle stream of hydrogen (26 kmoles per hour), carbon monoxide (17 kmoles per hour), carbon dioxide (227 kmoles per hour), water (1 kmole per hour) and with a minor amount of methane (<1 kmole per hour) is passed to a pre-reformer where it is heated to >500° C. in the presence of a catalyst and in the presence of steam (60 kmoles per hour) to reform all organic compounds larger than methane. The gas then passes to an autothermal reformer wherein autothermal reforming occurs, through the addition of oxygen (76 kmoles per hour). The reforming produces a product stream consisting of hydrogen (110 kmoles per hour), carbon monoxide (182 kmoles per hour), carbon dioxide (162 kmoles per hour), water (178 kmoles per hour) and a minor amount of methane (<1 kmole per hour) in the vapour phase. The initial product stream is cooled and the majority of the water (175 kmoles per hour) is separated to leave a first product stream comprising the remaining components (separation not shown in FIG. 1). Both the separated water and the first product stream are then passed to the fermentation step (total feed same as product stream from reforming), wherein fermentation occurs to produce 2 product streams:
a gas stream (8) consisting of hydrogen (28 kmoles per hour), carbon monoxide (18 kmoles per hour), carbon dioxide (245 kmoles per hour) and a minor amount of methane (<1 kmole per hour).
a liquid stream consisting of water (137 kmoles per hour), ethanol (41 kmoles per hour).

Carbon dioxide (15 kmoles per hour) is required to be separated to maintain the required hydrogen to carbon oxides ratio in the recycle stream, and this purge of gas also results in removal of small quantities of hydrogen (2 kmoles per hour) and carbon monoxide (1 kmole per hour) to reflect the concentrations of each component in stream 8. The remaining components (hydrogen (26 kmoles per hour), carbon monoxide (17 kmoles per hour) and carbon dioxide (228 kmoles per hour), water (1 kmole per hour) and with a minor amount of methane (<1 kmole per hour)) are recycled to the reforming step.

Example 1

A feed of methane (100 kmoles per hour) is passed to a steam methane reformer with steam (285 kmoles per hour) and a recycle stream of hydrogen (92 kmoles per hour), carbon monoxide (19 kmoles per hour), carbon dioxide (181 kmoles per hour) and methane (2 kmoles per hour). The steam:$CO_2$ ratio in the reforming is 1.56:1. The reforming produces a product stream consisting of hydrogen (318 kmoles per hour), carbon monoxide (193 kmoles per hour), carbon dioxide (107 kmoles per hour), methane (2 kmoles per hour) and water (259 kmoles per hour) in the vapour phase. The product stream is cooled and the majority of the water (256 kmoles per hour) is separated from a first product stream comprising the remaining components (separation not shown in FIG. 1). Both the separated water and the first product stream are then passed to the fermentation step (total feed same as product stream from reforming), wherein fermentation occurs to produce 2 product streams
a gas stream consisting of hydrogen (231 kmoles per hour), carbon monoxide (19 kmoles per hour), carbon dioxide (194 kmoles per hour), methane (2 kmoles per hour), a liquid stream consisting of water (216 kmoles per hour) and ethanol (44 kmoles per hour).

The system results in excess hydrogen, and thus hydrogen (139 kmoles per hour) is separated via membrane separation. Membrane separations are imperfect and remove gases in the following order of preference $H_2>>CO_2>>CO$ so a minor amount of carbon dioxide (12 kmole per hour) is necessarily also removed with the hydrogen. The remaining components (hydrogen (92 kmoles per hour), carbon monoxide (19 kmoles per hour), carbon dioxide (181 kmoles per hour) and methane (2 kmoles per hour)) are recycled to the reforming step.

Example 1 demonstrates the advantages of using a non-oxidative reforming step. In particular, although both Example 1 and the Comparative Example feed the same amount of methane, Example 1 generates more ethanol as well as an amount of hydrogen that can be usefully separated and utilised as fuel gas.

Example 2

A feed of methane (100 kmoles per hour) is passed to a steam methane reformer with steam (70 kmoles per hour) and a recycle stream of hydrogen (82 kmoles per hour), carbon monoxide (20 kmoles per hour), carbon dioxide (109 kmoles per hour) and methane (20 kmoles per hour). The steam:$CO_2$ ratio in the reforming is 0.65:1. The reforming produces a product stream consisting of hydrogen (298 kmoles per hour), carbon monoxide (205 kmoles per hour), carbon dioxide (25 kmoles per hour), methane (20 kmoles per hour) and water (54 kmoles per hour) in the vapour phase. The product stream is cooled and the majority of the water (51 kmoles per hour) is separated from a first product stream comprising the remaining components (separation not shown in FIG. 1). Both the separated water and the first product stream are then passed to the fermentation step (total feed same as product stream from reforming), wherein fermentation occurs to produce 2 product streams a gas product stream consisting of hydrogen (206 kmoles per hour), carbon monoxide (20 kmoles per hour), carbon dioxide (117 kmoles per hour), methane (20 kmoles per hour) and small quantities of water and ethanol a liquid stream consisting of 46 kmoles of ethanol and 8 kmoles of water.

Hydrogen (124 kmoles per hour) is separated via membrane separation from the gas stream. As in example 1, a minor amount of carbon dioxide (7 kmole per hour) is also removed with the hydrogen. The remaining components (hydrogen (82 kmoles per hour), carbon monoxide (20 kmoles per hour), carbon dioxide (109 kmoles per hour) and methane (20 kmoles per hour) are recycled to the reforming step.

Example 2 has the same advantages as Example 1 compared to the Comparative Example, but also demonstrates the advantages of reduced steam in the reforming step compared to Example 1. In particular, although both Examples 1 and 2 feed the same amount of methane, Example 2 generates slightly more ethanol. Although slightly less hydrogen is separated for fuel gas in Example 2, in fact the lower requirement for steam in the reformer means that hydrogen combustion as fuel can contribute a greater percentage of the reformer heating duty than is the case for Example 1.

Finally, not only is significantly less steam required to be provided for the reforming step of Example 2, but the steady state concentrations of carbon dioxide in the process is also less compared to Example 1, meaning that the total inventory of components passed into the reforming step is reduced from 680 kmoles per hour to 402 kmoles per hour, the total inventory of components passed into the fermentation step is reduced from 880 kmoles per hour to 602 kmoles per hour, and the total inventory of the recycle stream flow is reduced from 295 kmoles per hour to 232 kmoles per hour.

A particular advantage of the process of the present invention is that the $CO_2$ emissions from the overall process are considerably reduced, particularly in the case of dry reforming. The $CO_2$ emissions from the SMR with relatively high steam use are similar or lower than the ATR but the dry reforming flowsheet is clearly advantaged.

In particular, the following values have been estimated (based on energy requirements and any net $CO_2$ production):

$CO_2$ emissions from ATR process are estimated as 0.52-0.75 Te $CO_2$ per Te $C_2H_5OH$ (Including energy requirements for oxygen production and net $CO_2$ production. The lower limit assumes that the hot syngas provides enough heat for any pre-reformer that may be present, and the upper limit applies if a pre-reformer is present and requires external firing)

$CO_2$ emissions from the SMR process are estimated as 0.6 Te $CO_2$ per Te $C_2H_5OH$ (The principle reason for the increase over dry reforming is the increased reformer duty due to the steam and the increased recycle flow (more $CO_2$ as needs more driving force in the reformer to incorporate the steam)

$CO_2$ emissions from the dry gas reforming case are estimated as 0.33 Te $CO_2$ per Te $C_2H_5OH$.

The invention claimed is:

1. A process for the production of C2+ alcohols from a methane-containing feedstock, which process comprises:
   (a) passing said methane-containing feedstock and carbon dioxide to a non-oxidative reforming process to produce a first product stream comprising CO, $H_2$ and $CO_2$, optionally in the presence of steam, but with the proviso that where steam is present in the feed to the reforming process the steam and $CO_2$ are present in a molar ratio of less than 5:1,
   (b) passing the first product stream comprising CO, $H_2$ and $CO_2$ to a bacterial fermentation step wherein it is converted to produce a second product stream comprising one or more C2+ alcohols in the liquid phase and a gaseous third product stream comprising CO, $H_2$ and $CO_2$, the fermentation step being operated to provide a conversion of CO of at least 60%,
   wherein CO, $H_2$ and $CO_2$ are recycled from the gaseous third product stream to the reforming process of step (a) wherein at least 80% of the CO and 80% of the $CO_2$ in the gaseous third stream are recycled to the reforming process, and wherein the $H_2$ reacts with carbon dioxide in the reforming process.

2. A process as claimed in claim 1 wherein the reforming process is dry-gas reforming or steam methane reforming.

3. A process as claimed in claim 2 wherein the reforming process is a sulphur passivated reforming.

4. A process as claimed in claim 1 wherein no specific separation of carbon monoxide from carbon dioxide in the product stream is performed prior to recycle.

5. A process as claimed in claim 1 wherein some of the hydrogen in the gaseous third product stream is separated and utilised as a fuel gas.

6. A process as claimed in claim 1 wherein, where steam is present, the steam:$CO_2$ molar ratio is <1:1.

7. A process as claimed in claim 1 wherein both the reforming and fermentation steps are operated at a pressure is in the range 2 to 12 barg.

8. A process as claimed in claim 1 wherein a purge is taken from the recycled stream to prevent build-up of inerts.

9. A process as claimed in claim 1 wherein the fermentation process uses acetogenic anaerobic bacteria.

10. A process as claimed in claim 9 wherein the bacteria is selected from *Acetogenium kivui, Acetobacterium woodii, Acetoanaerobium noterae, Clostridium Aceticum, Butyribacterium methylotrophicum, Clostridium acetobutylicum, Clostridium thermoaceticum, Eubacterium limosum, Peptostreptococcus productus, Clostridium ljungdahlii* and *Clostridium carboxydivorans.*

11. A process as claimed in claim 10 wherein the bacteria is *Clostridium ljungdahlii.*

12. A process as claimed in claim 11 wherein the *Clostridium ljungdahlii* strain is selected from *Clostridium ljungdahlii* PETC, *Clostridium ljungdahlii* ERI2, *Clostridium ljungdahlii* C01, *Clostridium ljungdahlii* O-52.

* * * * *